(12) United States Patent
Gitis et al.

(10) Patent No.: US 6,573,836 B1
(45) Date of Patent: Jun. 3, 2003

(54) METHOD AND APPARATUS FOR DETECTING THE PRESENCE OF POWDERED MATERIAL IN ENVELOPES

(75) Inventors: Norm Gitis, Cupertino, CA (US); Rashid Mavliev, Santa Clara, CA (US); Alex Meyman, Belmont, CA (US); Oleg Shulepov, Santa Clara, CA (US)

(73) Assignee: Nevmet Corporation, Reno, NV (US)

( * ) Notice: Subject to any disclaimer, the term of this patent is extended or adjusted under 35 U.S.C. 154(b) by 0 days.

(21) Appl. No.: 10/035,967

(22) Filed: Jan. 4, 2002

(51) Int. Cl.[7] ............................................... G08B 21/00
(52) U.S. Cl. .................... 340/603; 340/540; 73/863.22; 73/52
(58) Field of Search ................................ 340/612, 632, 340/627, 603, 540; 73/863.22, 52, 863.85, 864.21, 864.51, 864.91, 866, 432.1; 209/900, 552, 591

(56) References Cited

U.S. PATENT DOCUMENTS

| 5,212,993 | A | * | 5/1993 | Mayer | ...................... 73/864.21 |
| 6,267,016 | B1 | * | 7/2001 | Call et al. | ................. 73/863.22 |
| 6,363,800 | B1 | * | 4/2002 | Call et al. | ................. 73/863.22 |
| 2001/0029793 | A1 | * | 10/2001 | Moler et al. | .............. 73/863.22 |
| 2002/0124664 | A1 | * | 9/2002 | Call et al. | ................ 73/863.22 |
| 2002/0126008 | A1 | * | 9/2002 | Lopez et al. | ................. 340/540 |
| 2002/0141613 | A1 | * | 10/2002 | Sansone | ...................... 382/101 |

OTHER PUBLICATIONS

Plasma Sol Corp. makes news in war against anthrax (http://stevensnewsservice.com/PR215.htm).
SmartCycler—Bacteria Detection Device (http://www.smartcycler.com/pages/works.html).

* cited by examiner

Primary Examiner—Daniel J. Wu
Assistant Examiner—Sihong Huang

(57) ABSTRACT

An apparatus for detecting the presence of powdered materials in envelopes comprises a container with an envelope-positioning unit, envelope corner or edge cutter, a powder excitation and extracting means for shaking the contents of the envelope, and a powder detector with a particle intake device, and air circulation system for circulation of the particle-containing air through the powder detector. The detector can be placed inside or outside of the sealed container and is connected to the cutting zone via the particle suction device. In operation, the envelope is placed into the envelope-positioning unit. Either a corner or an edge of the envelope is cut off or perforated so as to allow a part of the powdered material to leave the envelope while maintaining the other contents, except for small particulates, intact and inside the envelope. The envelope is then subjected to vibration or impacts under the effect of the excitation means. In case of detection of a hazardous material, the apparatus will produce alarm signals and will lock the door to restrict access to the apparatus.

40 Claims, 14 Drawing Sheets

METHOD AND APPARATUS FOR DETECTING THE PRESENCE OF POWDERED MATERIAL IN ENVELOPES

FIELD OF THE INVENTION

The present invention relates to a method and apparatus for detecting the presence of powdered materials in closed envelopes, in particular, for detecting powdered infectious, contagious, contaminating, or other undesired substances that can be sent via mail.

BACKGROUND OF THE INVENTION

Recent increase in the acts of terrorism, in particular, of bio- and chemical terrorism, caused US Government to undertake development of new reliable and rapid-response measures for dealing with the suspicious substances in the mail, which appeared to be one of convenient channel for delivery of contagious bio- and chemical substances to governmental offices, companies, and individuals. One such measure is irradiation of mail started by the U.S. Postal Service in response to anthrax mail contamination that has been found on Capitol Hill, in White House Postal Service, in offices of senators, and in other locations. Contaminated mail has sickened more than a dozen people and claimed the lives of postal workers at some mail sorting centers.

PlasmaSol Corp., N.J., has developed "nonthermal plasma" that emits germ-killing ultraviolet rays and creates ozone that oxidizes chemicals and bacteria like a disinfectant. This device can work under normal atmosphere and therefore do s not require the use of complicated and expensive vacuum and vacuum-sealing equipment. Tests on the anthrax-like bacteria have generated positive results. However, regular envelopes are not transparent, and thus high doses of ultraviolet irradiation are required, which limits its practical use.

Total irradiation of the entire mail circulating through the United States may be an unreal objective in view of its high cost and extremely small amount of contaminated mail as compared to millions of items circulating daily through the channels of the U.S. Postal Service. High radiation doses needed for decontamination of bacteriological particles require expensive protection of and highly qualified personnel working with this equipment at postal facilities. Also, maintenance of the mail irradiation equipment will be no less expensive than its operation.

In view of the sporadic and random distribution of contaminations mail, it would be more appropriate to conduct selective screening at the mail destination locations only of those letters and packages that seem suspicious. However, since the United States were taken with the acts of bio-terrorism by surprise, this country has not yet developed reliable equipment for the solution of the above problem.

In fact, some specialized biological agent detection devices existed in the civil defense system. For example, in 1994 the Department of Defense disclosed the existence of almost 40 Biological Integrated Detection Systems (BIDS) designed for Army. However, all these systems were intended for battlefield conditions and had not been introduced into practical use, due to no demand for such use. Nevertheless, at the present time BIDS uses off-the-shelf instrumentation, including an aerosol-particle counter/sizer, a bioluminescence analyzer, a liquid-particle counter/sizer, a particle sampler, and a manual antibody-based detector. Among the agents that BIDS is required to detect and identify are anthrax and plague bacteria, botulinal toxin A, and staphylococcal enterotoxin B.

In response to the recent anthrax menace, some commercial companies have developed and are selling on-site detection kits for anthrax, as fears of the often-lethal bacteria spread across the country. One example of such bacteria-detection equipment is Smart Cycler, produced by a private company Cepheid, California. This device combines optical spectroscopy with fluorescent analysis and makes it possible to detect anthrax and other hazardous biological substances.

Although the Smart Cycler operates reliably and efficiently, it is only a detection device, which requires a special procedure for preparation of test samples. Furthermore, this device, like any other detector, requires preliminary revealing of suspicious objects, e.g., closed postal envelopes with suspicious contents. It is well known that in majority of cases the biological contaminants comprise fine powders, which are convenient for delivery through mail and which immediately scatter in air when the envelope is opened. Thus, prior to detecting and defining the suspicious powder, it is necessary to reveal a suspicious envelope, to open it under conditions safe for the personnel, and to test the interior of the envelope for the presence of a powder, irrespective of whether this powder is contagious or neutral, and only in the case the powder is found, it is then detected and analyzed in such a device as Smart Cycler. However, at the present time none such equipment, suitable for use in facilities receiving from several to thousands letters per day, is available.

OBJECTS AND SUMMARY OF THE INVENTION

It is an object of the invention to provide a method and apparatus for revealing mail with suspicious contents as a measure of preliminary presorting of closed postal envelopes and for making the mail with suspicious substances available for a further detailed analysis. It is another object to provide the aforementioned apparatus, which is simple in construction, inexpensive to manufacture, simple and safe in use, and incorporates a commercially produced particle detector. It is another object of the invention to provide the aforementioned apparatus, which is equipped with an electronic control unit that controls operation of a cutter, envelope excitation means, alarm and locking devices. It is another object to provide the aforementioned apparatus and method suitable for use in mailrooms of enterprises, companies and establishments that daily receive from several to thousands items of mail.

An apparatus of the invention for detecting the presence of powdered materials in closed envelopes comprises a sealed container provided with a loading/unloading port, an envelope-positioning unit, envelope corner or edge cutter, a powder excitation and extraction unit for exciting the contents of the envelope, and a powder detector with a particle intake device, and an air circulation system for circulation of the particle-containing air through the powder detector. The detector can be placed inside or outside of the sealed container and is connected to the cutting zone via the particle suction device. In operation, each piece of the selected suspicious mail is placed into the envelope-positioning unit that can be located inside the container, e.g., on the backside of the door, so that either a corner or an edge of the envelope is aligned with the position of the cutter. The door is closed for sealing the container with the envelope to be tested. The corner or the narrow edge of the envelope is cut off or perforated so as to allow the powdered material to come out from the envelope while maintaining the other contents, except for small particulates, intact and inside the envelope. The envelope is then subjected to either vibrations or impacts under the effect of the excitation and extraction device. If the envelope contains any fine powdered material, the vibrations will excite the fine powdered particles, which begin to move. This will cause the powder to leave the envelope through the opening formed in the cut-off corner or edge perforations of the envelope. The particles suspended in air underneath the envelope corner will be sucked into the particle intake device and delivered to the powder detector. The results of particle analysis can be displayed or recorded, as well as analyzed by a control unit, while the air exhausted from the powder detector will return to the container and will circulate through the above-described path. The judgment on the presence of the suspicious substance will be made by comparing the measured data with a predetermined reference threshold. The maximum threshold value for the number of particles unloaded from a single envelope is selected based on real conditions, according to which the detector will produce an alarm signal if the number of particles will exceed the predetermined threshold. In case of detection of a hazardous material, the apparatus will produce both sound and visible alarm signals, at the same time locking the door to prevent access to the apparatus for unauthorized personnel.

DETAILED DESCRIPTION OF THE INVENTION

Figure 1:
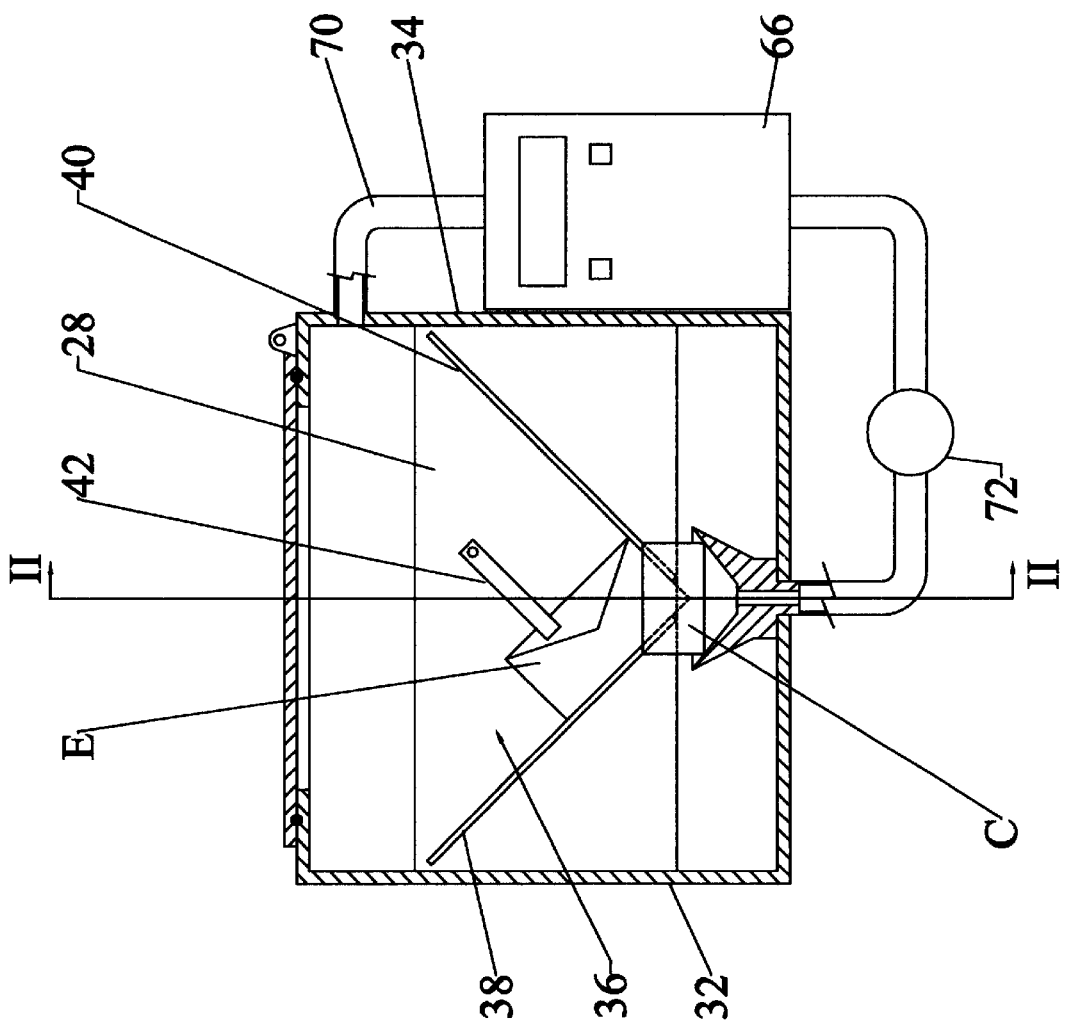
FIG. 1 is a front vertical sectional view of the apparatus of the invention.
Figure 2:
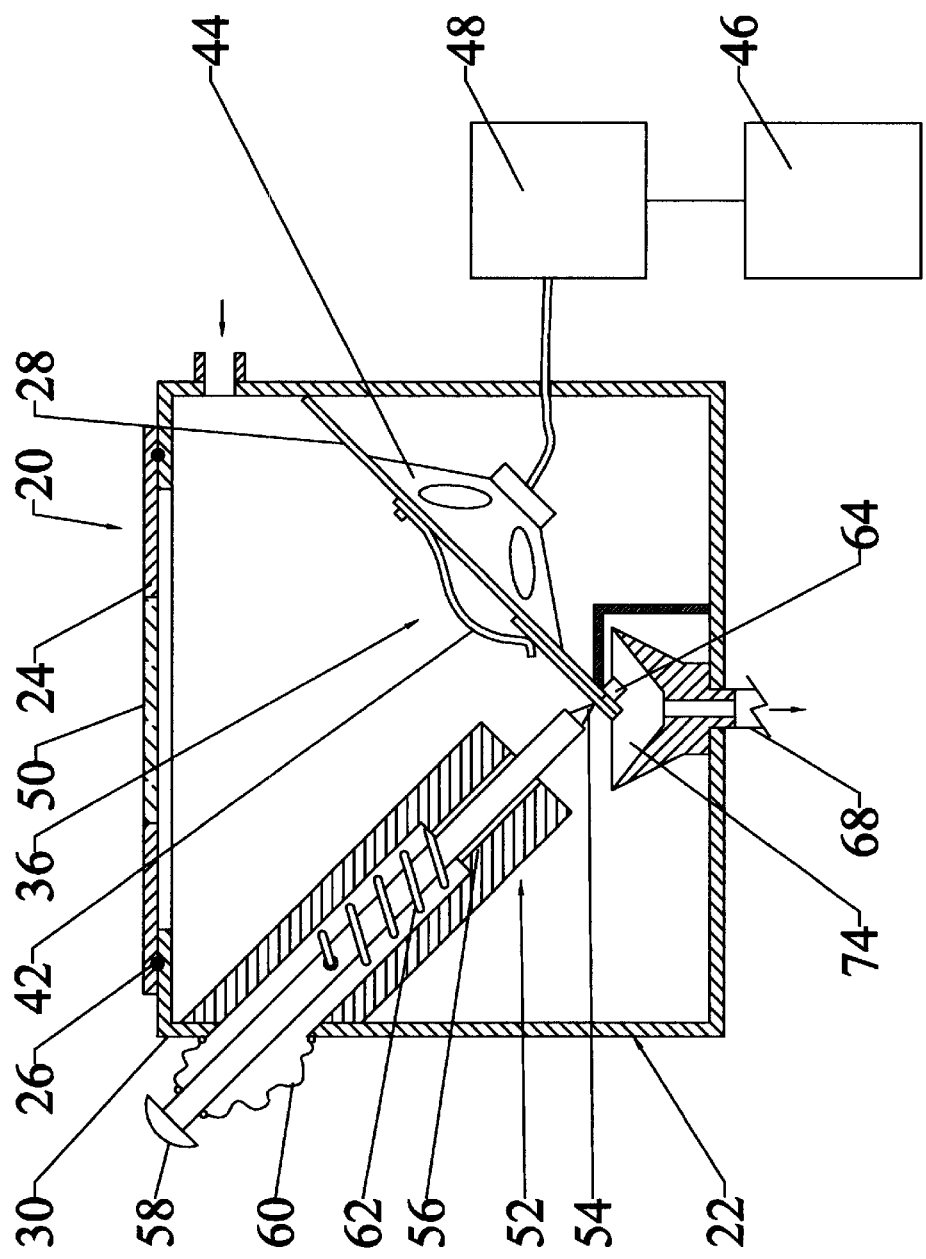
FIG. 2 is a sectional view along the line II—II of FIG. 1 illustrating position of the powder excitation and envelope material remover devices.

An apparatus made in accordance with one embodiment of the invention is shown in FIGS. 1 and 2. Here FIG. 1 is a front vertical sectional view of the apparatus of the invention. FIG. 2 is a sectional view along the line II—II of FIG. 1, illustrating position of the particle excitation and extraction unit and the cutter.

In the context of the present invention, the term "powdered material" covers any substance in the form of coarse, fine, or very fine particles from millimeters to nanometers. This term covers powders and powder-like materials, e.g., in the form of thin short fibers, or the like.

In the context of the present invention the term "envelope" covers various pieces of mail or delivery including letter, parcels, etc. In the context of the present invention, the term "closed envelope" means that the envelope protects its contents from unauthorized observation, even though the corner or the edge of the envelope is cut off or perforated.

As can be seen from FIGS. 1 and 2, the apparatus, which in general is designated by reference numeral 20, consists of a container 22 having a cover 24 located at the top of the container 22 and capable of closing the container 22 so that the interior of the container is sealed by a seal element 26. As can be seen from FIG. 2, the rear wall 28 is inclined with respect to a vertical front wall 30 and vertical side walls 32 and 34 of the container. All the walls of the container should maintain the interior of the container tightly sealed when the cover 24 is closed. On its front side, the inclined rear wall 28 of the container 22 supports an envelope-positioning unit 36. As can be seen from FIGS. 1 and 2, the envelope-positioning unit 36 is made in the form of a trough composed of two inclined plates 38 and 40, which are substantially perpendicular to the rear wall 28 and to each other. However, as can be seen from FIG. 1, the converging ends of the inclined plates 38 and 40 do not intersect in an apex point but rather are discontinued at some distance from the apex so that a space is left for protrusion of the envelope corner when the envelope E is inserted into the envelope-positioning unit 36, as shown in FIG. 1. Reference numeral 42 designates a spring-like clamp for securing the envelope E inside the envelope-positioning unit 36.

The rear wall 28 is made of a resilient material, such as a spring-type stainless steel so that this wall could function as a resilient membrane. On its backside (FIG. 2), the rear wall supports an excitation and extraction unit 44, e.g., in the form of an acoustic loudspeaker, so that the acoustic waves generated by the loudspeaker 44 will cause the rear wall 28 to vibrate. The powder excitation and extraction unit causes at least a part of the powder material to separate from the envelope and to leave the envelope with an air flow through the opening produced by cutting. The loudspeaker 44 is provided with an either single-pulse or a.c. generator 46 located outside the apparatus 20, which is connected to the loudspeaker 44 via an amplifier 48. The loudspeaker 44 is rigidly connected to the backside of the rear wall 28. The generator 46 may generate either single pulses or alternating current with frequency from several Hz to several kHz. The alternating current can be generated in a continuous, intermittent or programmed mode selected for optimization of conditions required for excitation and extraction of powder that may be contained in the envelope. The amplitude of the oscillations can be controlled via the amplifier 48.

The container 22 may have a transparent window 50, which in FIG. 2 is shown in the cover 24, though the window can be formed in any other wall of the container 22.

In the area of the envelope-positioning unit 36 open for protrusion of the envelope end, e.g., corner C (FIG. 1), the apparatus 20 is provided with an envelope end remover 52. In FIG. 2, the remover 52 is schematically shown in the form of a cutter blade 54 provided on the end of the remover and reciprocating in guides 56 fixed in the container. A handle 58 projects outside the container 22 through the front wall 30 of the container. Bellows 60 are used for sealing the interior of the container from the projecting end of the remover 52. A return spring 62 automatically lifts up the blade 54 from the envelope after the cut is completed. Pushing on the handle 58 starts cutting of the envelope corner. A clump 64 that functions as a support for the corner C of the envelope E during cutting can be provided in the trough against the cutting blade 54.

On its way towards the envelope, the handle 58 engages an excitation switch (not shown) that activates the generator 46, and thus causes the loudspeaker 44 to vibrate and shake the rear wall 28 of the container 22.

The particle detection system consists of a particle detection unit 66 (FIG. 1), sealingly connected to the interior of the container 22 via a particle intake suction pipe 68, and a return pipe 70 for returning the air from the powder detector back to the interior of the container 22 for recirculation. As can be seen from FIGS. 1 and 2, for convenient entrance of particles, the suction port of the particle intake suction pipe 68, which is inserted into the interior of the container underneath the area where the corner of the envelope E is to be located, may have a funnel-like shape. A vacuum pump 72 is installed in the particle intake suction pipe 68 for suction of particle-carrying air and for the supply thereof to the powder detector 66. The particle intake pipe 68 has a replaceable and disposable suction cup 74 that can be easily replaced. In order to facilitate sterilization of the interior of the container 22, the inner walls of the container 22 should be smooth with rounded corners.

Powder detector 66 can be selected from a group consisting of a particle counter counting the number of powder material particles, particle geometry analyzer analyzing the geometry of powder material particles, particle physical analyzer analyzing the physical properties of powder material particles, and particle chemical analyzer analyzing the chemical properties of powder material particles. Examples of commercially available airborne particle detectors suitable for use in conjunction with the apparatus of the invention are devices produced by Japanese company Rion Corporation, models KC20, KC-01D1, and KC-03A1. This device is based on optical scattering, has a suction unit with capacity of 30 liter/min, has an alarm function. It can detect particles of different sizes from 0.3 to 100 microns, in concentration from 0 to 2000 particles/liter. This device and its models are given only as an example.

The apparatus of the embodiment shown in FIGS. 1 and 2 operates as follows.

It is understood that the apparatus of the invention can be used for checking the entire mail, if volume of the mail allows such treatment, or selectively only for suspicious envelopes. For checking an envelope E (FIG. 1), the cover 24 of the container 22 is opened, and the envelope E is placed into the envelope-positioning unit 36 so that the envelope corner C is positioned in the cutting zone of the cutting blade 54. The cover 24 is then closed so that the interior of the container 22 is sealed from the surrounding environment. The interior of the container 22 is seen through the transparent window 50. The operator then activates the powder detector 66 so that the suction pump begins to suck air from the interior of the container 22 and to supply it to the powder detector 66. The operator pushes on the spring-loaded handle 58 of the cutter 52 whereby the cutter blade 54 cuts off the envelope corner C. Pushing on the handle 58 closes the contacts of the above-described excitation switch, whereby the envelope excitation device 44 is activated. If necessary, prior to operation, the generator 46 can be adjusted with regard to the frequency of pulsing impacts or oscillations in order to select the optimal mode for the types of envelopes checked in the apparatus of the invention.

If the envelope E contains a powdered material, under the effect of excitation transmitted from the loudspeaker 44 to the rear wall 28 of the container that supports the envelope-positioning unit 36, the powdered material will pour out from the envelope E through the opening in the envelope corner C. As a result of a suction force developed at the funnel-shaped intake suction pipe 68 by the action of the vacuum pump 72 of the powder detector 44, the powdered material will be sucked into the pipe 68 and delivered to the powder detector 44. Not only those particles of the powder that fall directly into the suction pipe enter the powder detector, but also airborne fine particles that are suspended in the space within the container will be drawn into the intake pipe 68 and hence into the powder detector 44.

Modern particle detectors, such as some of those produced by Rion Corporation and shown herein as an example of a detector suitable for the apparatus of the present embodiment, are capable of determining not only the number of particles received by the detector and counted in a unit volume of the sucked air, but also the dimensions of the particles and distribution over the dimensions. Data relating to the size and dimensional distribution of the particles in some cases can be used for determining the material of the powder, provided the powdered substance has very specific dimensions of particles and dimension dispersion. The dimension dispersion curves may be used for preliminary identification of the substance found in the envelope. More reliable detection of the powered materials can be conducted under laboratory conditions with the use of instruments such as the aforementioned Smart Cycler produced by a US company Cepheid, California.

The apparatus of the invention may be equipped with a mechanically driven envelope material remover. In the context of the present invention, "envelope material remover" is a general term that covers devices for separating a part of the envelope material from at least one envelope corner or at least one envelope edge in order to form an opening for extraction of powder materials from the inside the envelope. The envelope material remover can be a cutter, a punching or perforating device or the like.

Figure 3:
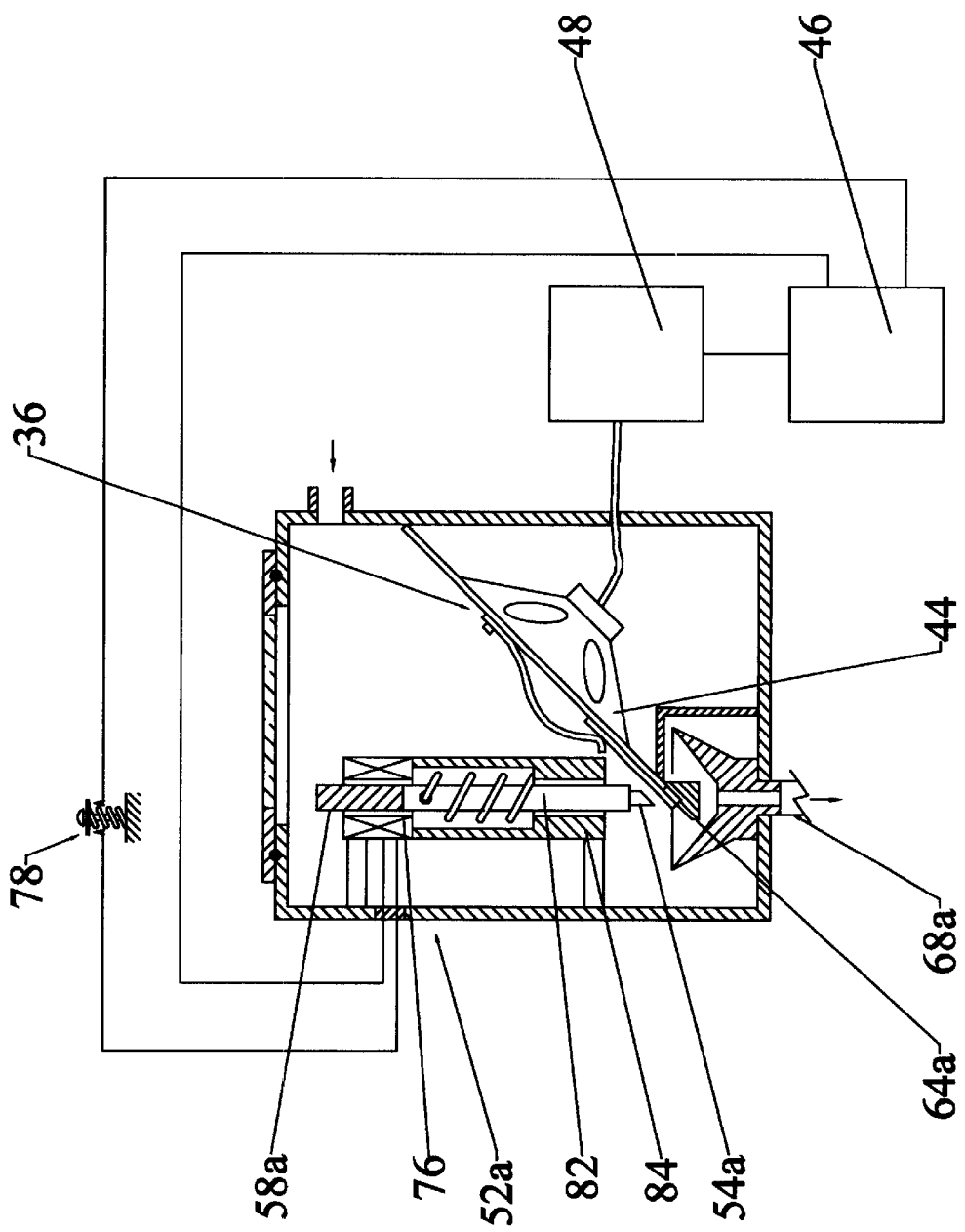
FIG. 3 is a schematic view of the embodiment of the apparatus of the invention with an electromagnetically driven envelope material remover and a loudspeaker-type powder excitation and extraction unit.

For example as shown in FIG. 3, the blade 54 can be driven electromagnetically with a solenoid core 58a which can be made from a magnetic material such as iron. The solenoid 76 can be activated by pushing on a push button or pedal 78 (FIG. 3). The cutter drive mechanism shown in FIG. 3 consists of a pushing rod 82 which is connected to the core 58a and guided in guide 84. The apparatus of the embodiment equipped with the electromagnetically driven cutter operates in the same manner as the apparatus with the manually driven cutter shown in FIGS. 1 and 2, with the exception that the cutter will be activated by pushing/pressing on the button/pedal 78.

Figure 4:
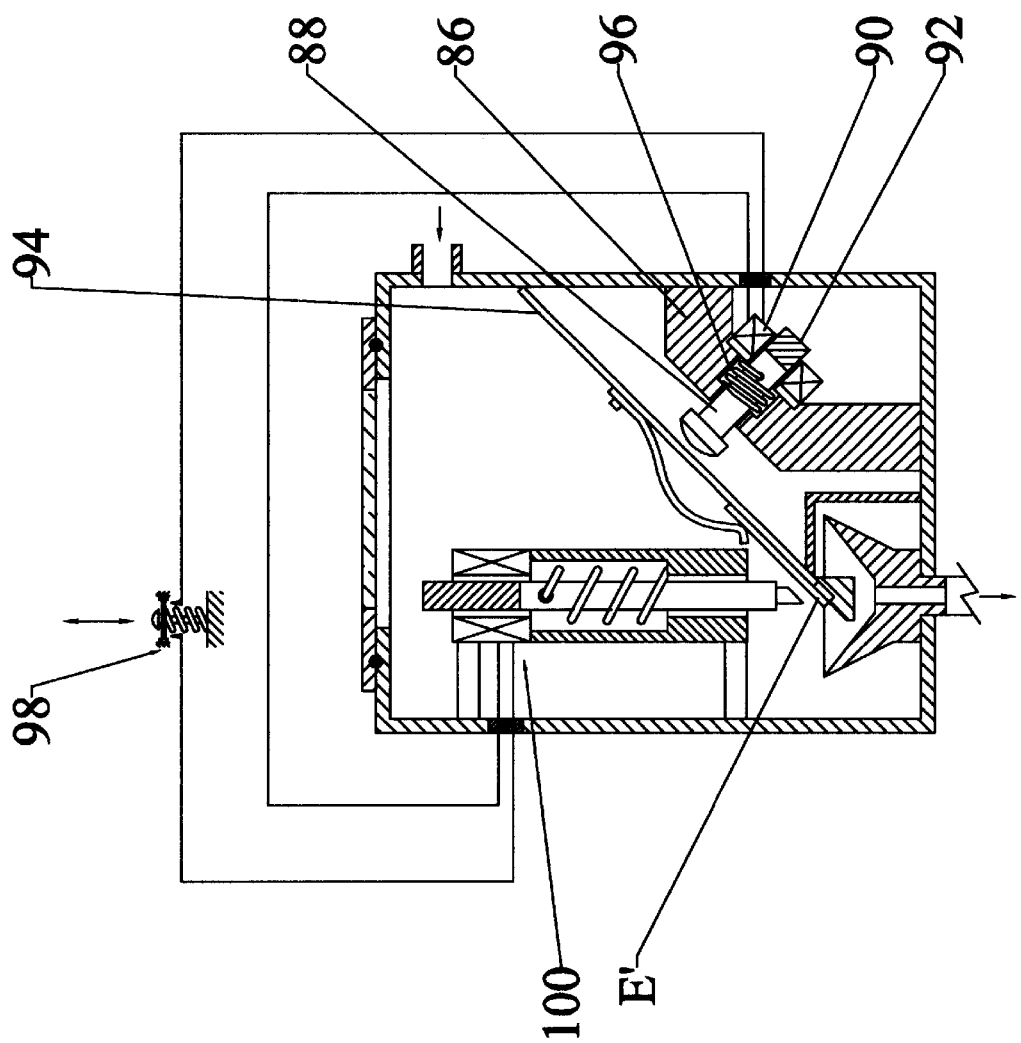
FIG. 4 illustrates an embodiment of the apparatus of the invention with an impact-type powder excitation device.

FIG. 4 illustrates another embodiment of the apparatus of the invention, in which a powder excitation and extraction unit 44, shown in FIGS. 2 and 3, is replaced by an impact-type excitation device 86. The excitation device 86 includes a plunger 88 driven with an electromagnetic coil 90. This coil interacts with the rear end of the plunger, which functions as a core 92 of the solenoid. When the coil 90 is activated, it pulls the plunger 88 away from the rear wall 94 and extends the spring 96. When the contacts 98 of the electromagnetic coil 90 are de-energized, the spring 96 returns the plunger towards the rear wall 94, whereby a blow is applied to this wall. The impact of this blow is transmitted to the rear wall 94 and hence to the envelope, whereby the contents of this envelope is shaken. This arrangement can be reversed so that the blow will be applied by the core and the spring will return the core to the initial position. Activation of the electromagnetic excitation device 86 can be interlocked with activation of the electromagnetic cutter 100 so that the corner of the envelope E' is cut simultaneously with application of impacts.

Figure 5:
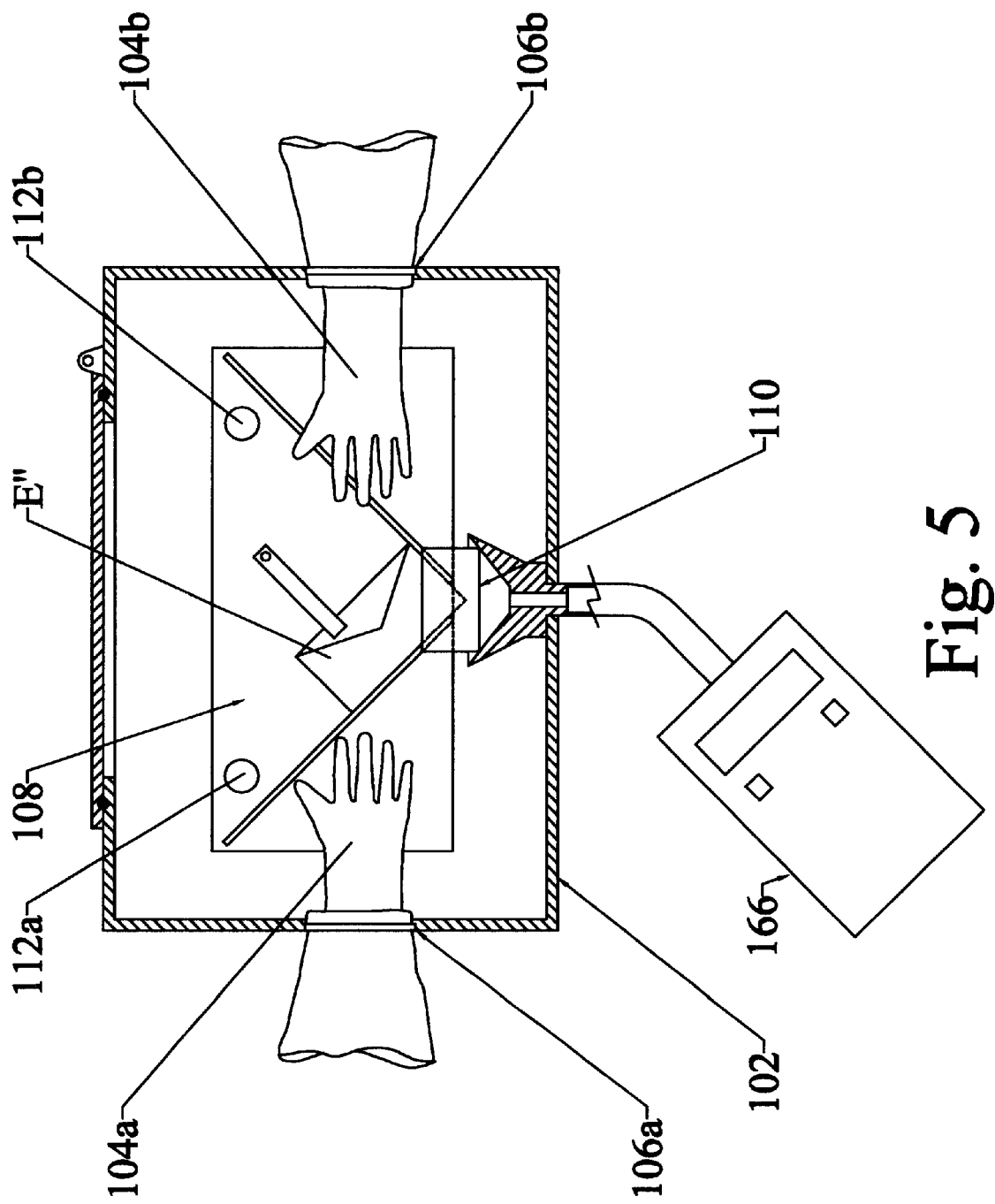
FIG. 5 illustrates a simplified embodiment of the invention, in which the envelopes are handled manually inside the sealed transparent container with the use of latex gloves.

FIG. 5 illustrates a simplified embodiment of the invention, in which the envelopes are handled manually inside the sealed transparent container 102 by means of latex gloves 104a and 104b inserted into the container 102 through sealing sleeves 106a and 106b. The gloves 104a and 104b can be inserted through the front or side walls of the container 102. The operator may use the gloves for manually positioning the envelope E" in the envelope-positioning unit 108, while the cutter 110 can be activated by pushing on buttons 112a and 112b. The two buttons are used in order to cause the operator to use both hands for activation of the envelope material remover. This is necessary for safety reasons in order to protect the operator's hands from the cutting action of the blade. Reference numeral 166 designates a powder detector.

Figure 6:
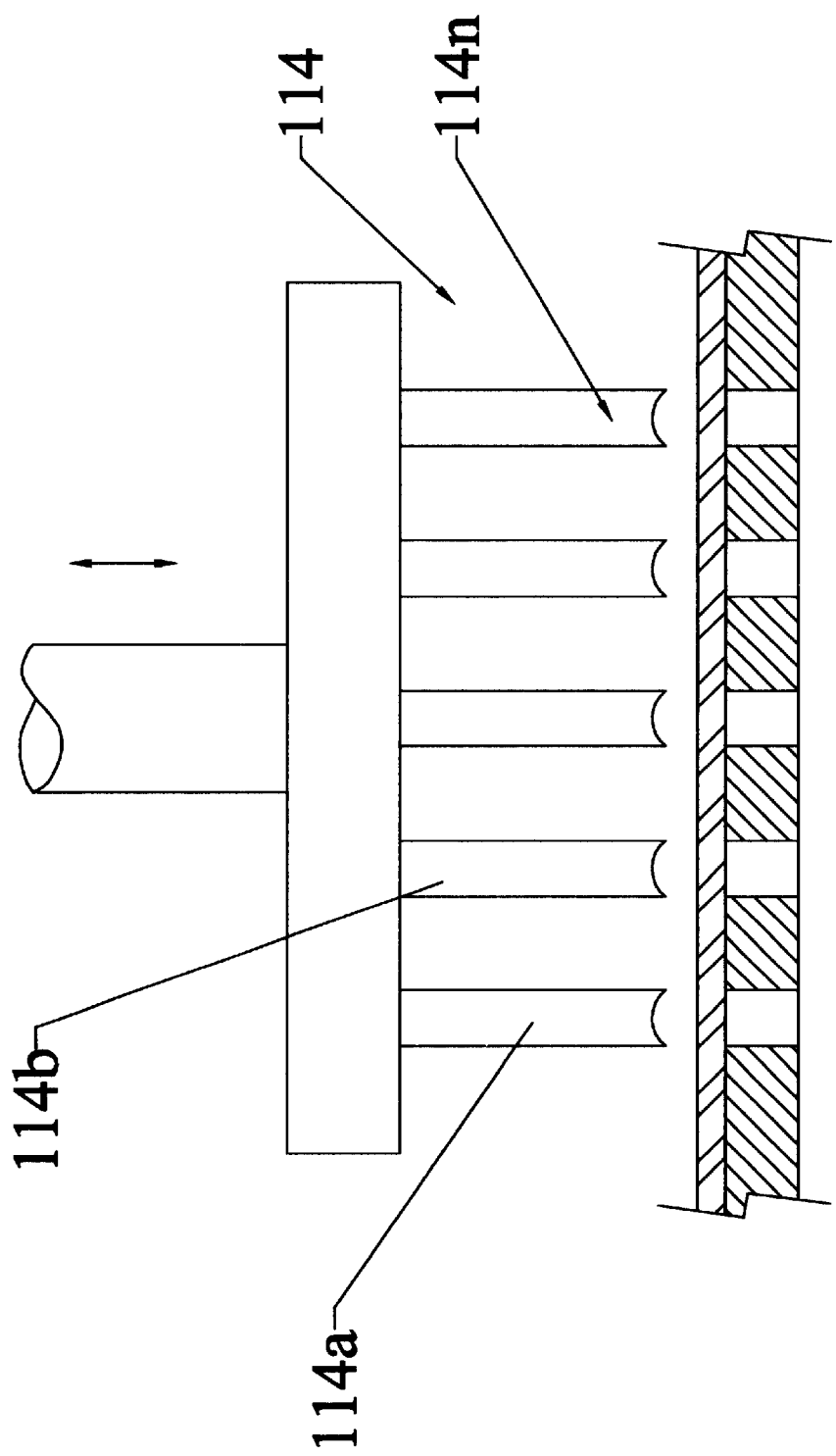
FIG. 6 is a view of a modified envelope material remover for perforating a narrow edge of the envelope.
Figure 7:
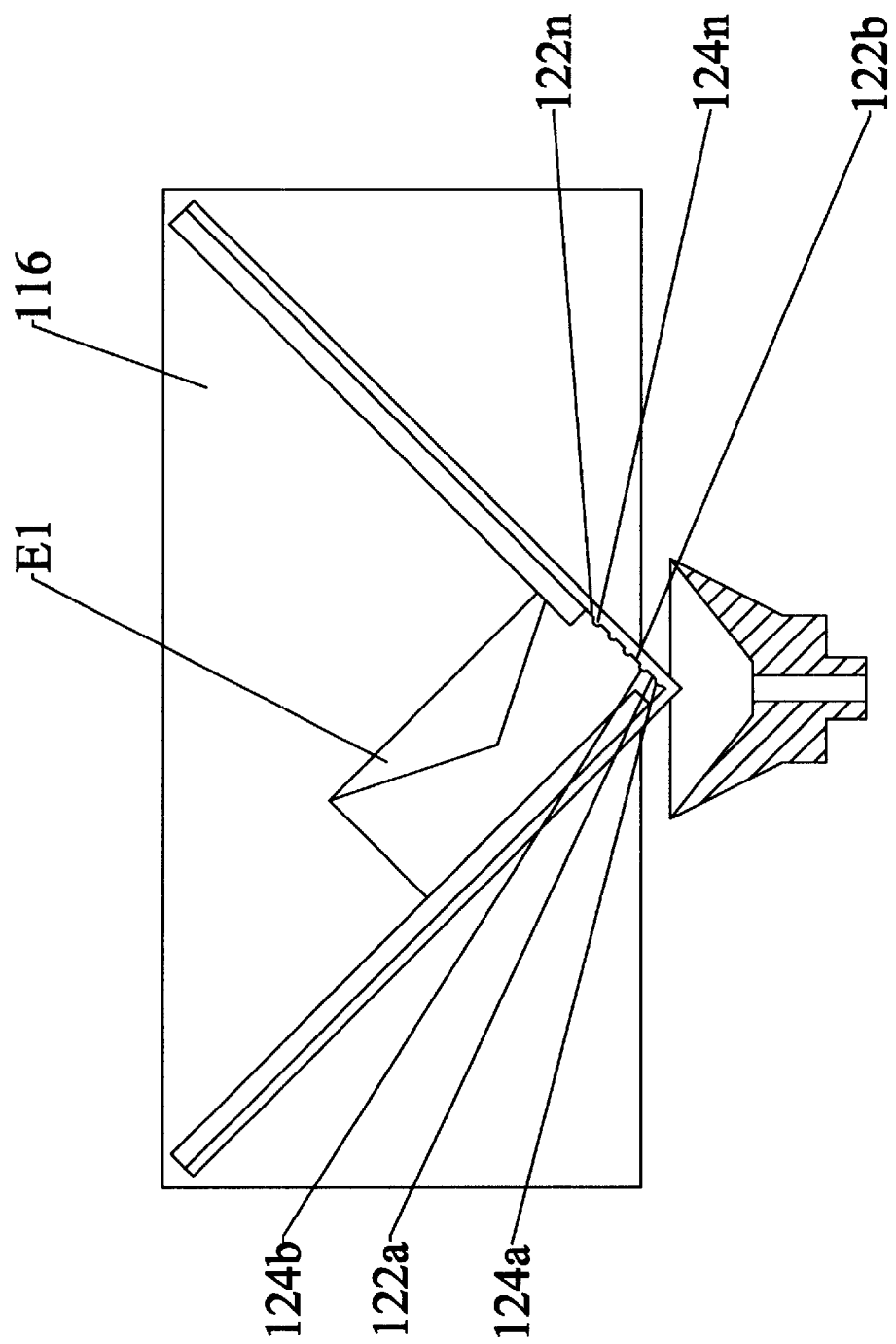
FIG. 7 is a fragmental view of the device of FIG. 6 with the perforated envelope.

FIGS. 6 and 7 show a modified shape of the envelope material remover 114 suitable for all previously described embodiments. In the embodiment of FIG. 6 the envelope material remover either cuts off or perforates or punches at least a part of at least one edge of the envelope. More specifically, the envelope material remover 114 has an intermittent cutting edge in the form of a plurality of cutting rods or punches 114a, 114b, ... 114n, that may have, e.g., a circular cross section. The rods 114a, 114b, ... 114n may have cutting edges similar to those in conventional paper punches. The envelope E1 is positioned in the envelope-positioning unit 116, which is inclined to the vertical similar the previous embodiments, so that the projection of the rods 114a, 114b, ... 114n onto the envelope overlap only a portion of the narrow envelope edge 118. The surface of the plate 119 (FIG. 7), which supports the envelope E1 in the envelope-positioning unit 116, has holes aligned with the positions of the rods so that during the cutting cycle, the punching rods will cut or punch only portions of the envelope edge 118 in a discrete manner so that after cutting the envelope will look as shown in FIG. 7 with a plurality of uncut portions 122a, 122b, ... 122n. These uncut portions will preserve the confidentiality of the mail. The perforated portions 124a, 124b, ... 124n formed in the envelope will allow the powder to come out from the envelope. This embodiment with the modified envelope material remover can be used in conjunction with the drives of the envelope material remover shown in any previous embodiment. In the embodiment of FIGS. 6 and 7 at least one edge 121 of the cut side of the envelope should be used for supporting and for positioning of the envelope with respect to the envelope material remover, while the remaining part 123 of the envelope side will be punched.

Figure 8:
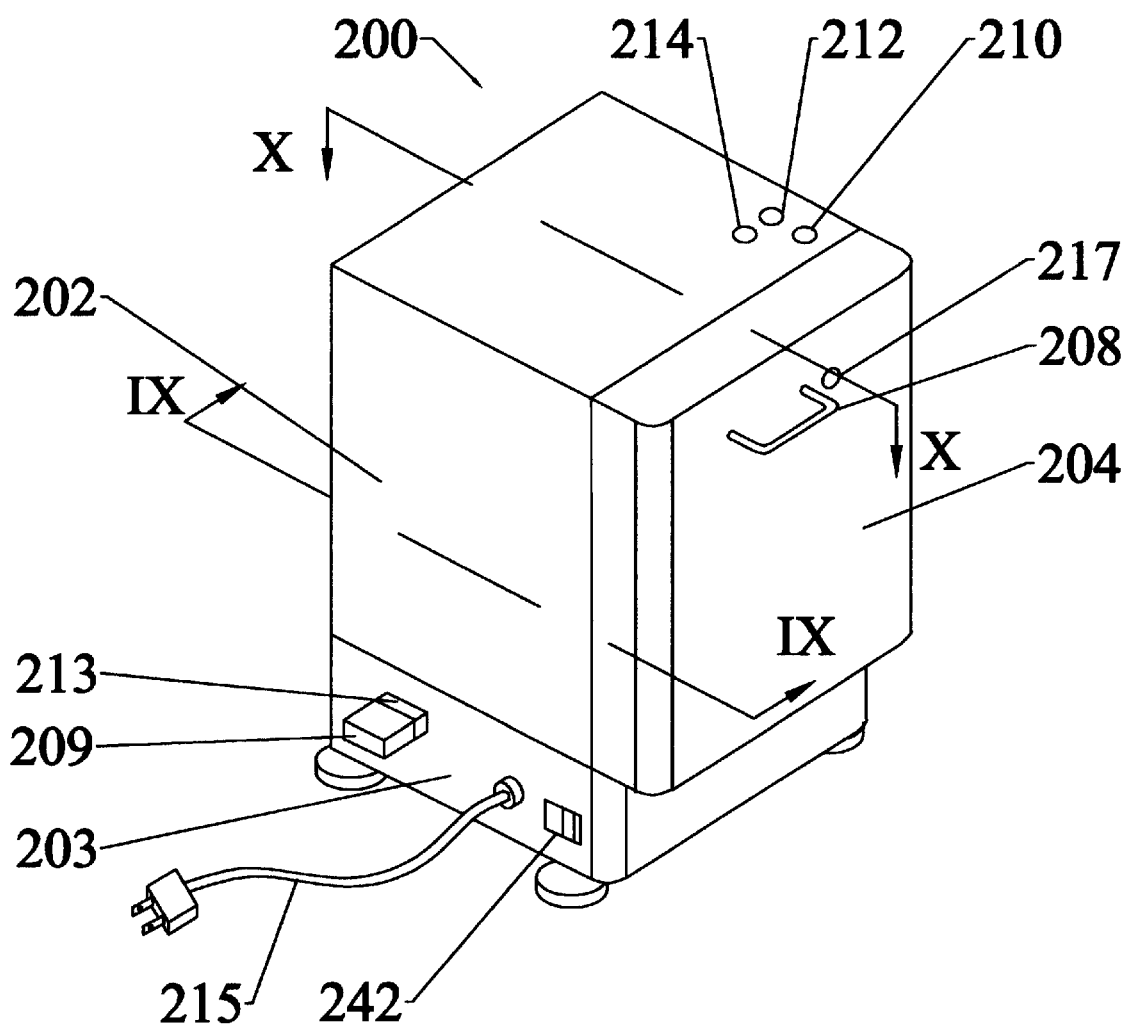
FIG. 8 in is a three-dimensional front view of the apparatus of the embodiment.

Another embodiment of the invention is shown in FIG. 8, which is a three-dimensional front view of the apparatus. The apparatus, which in general is designated by reference numeral 200, consists of a hollow rectangular container 202, the front side of which can be opened or closed by means of a door 204. Located beneath the container 202 is an electronic unit 203 which may be placed into a separate lower compartment of the container 202 or into a separate housing that may support the container 202. Other parts and elements seen on FIG. 8 are a door handle 208, a start button 210, an alarm indicator lamp (red) 212, and a normal operation status indicator lamp (green) 214. The start button 210 and indicator lamps can be located on the door 204 or on the top of the container 202. Reference numeral 242 designates an ON/OFF switch for electronics located on the electronics unit; 215 is a power supply cord.

Figure 9:
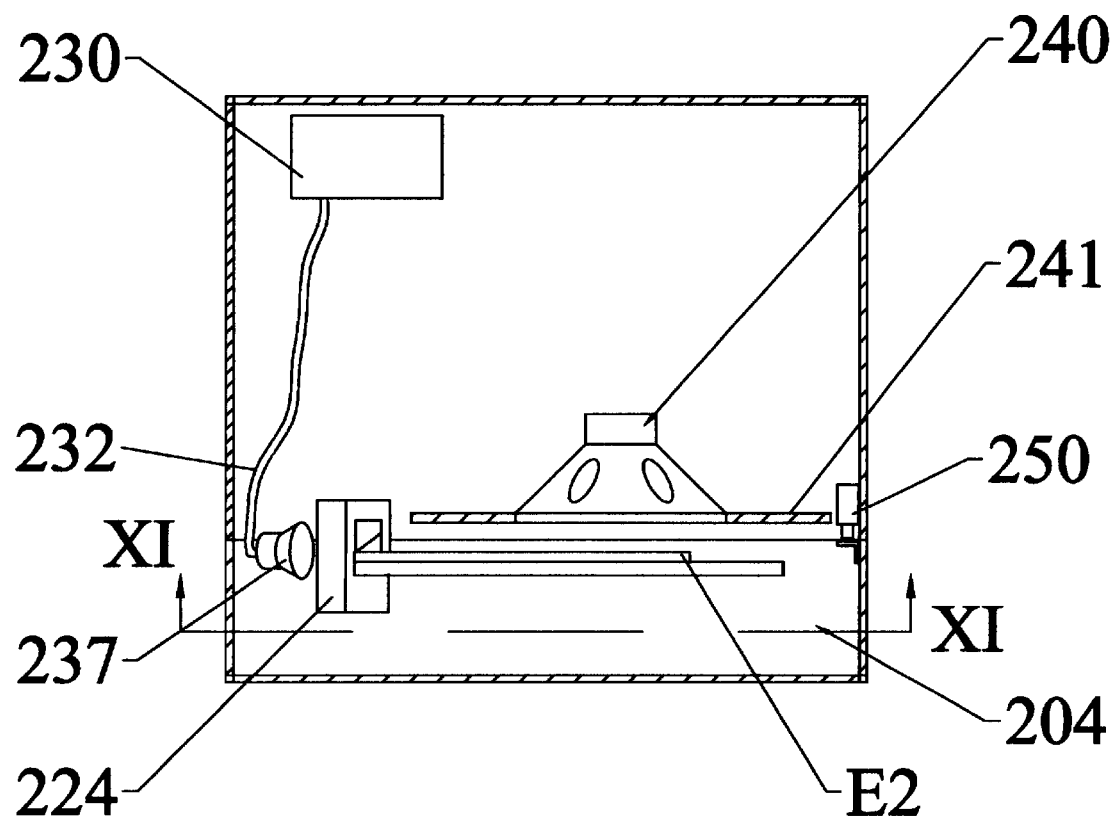
FIG. 9 is a top sectional view of the apparatus of FIG. 8 in the direction of arrows IX—IX.
Figure 10:
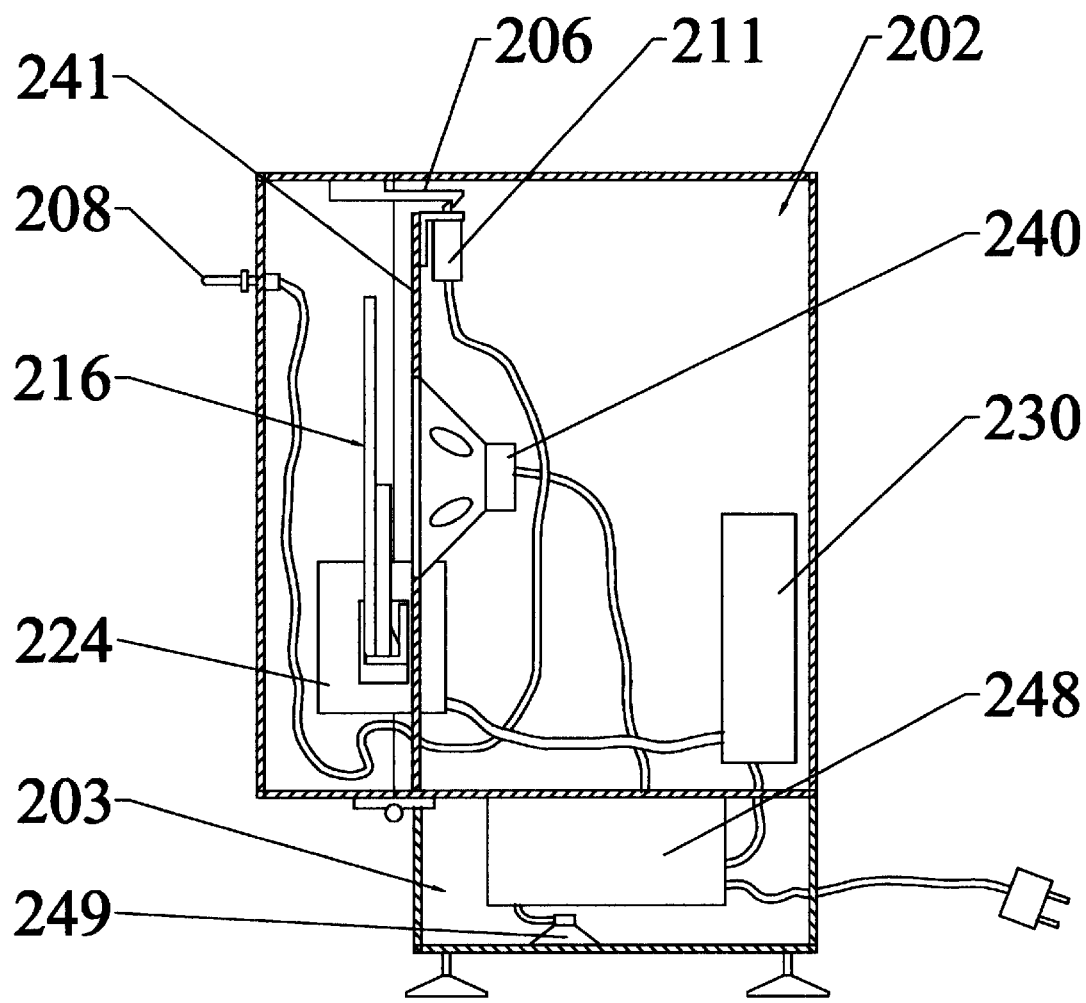
FIG. 10 is a side sectional view of the apparatus of FIG. 8 in the direction of arrows X—X.
Figure 11:
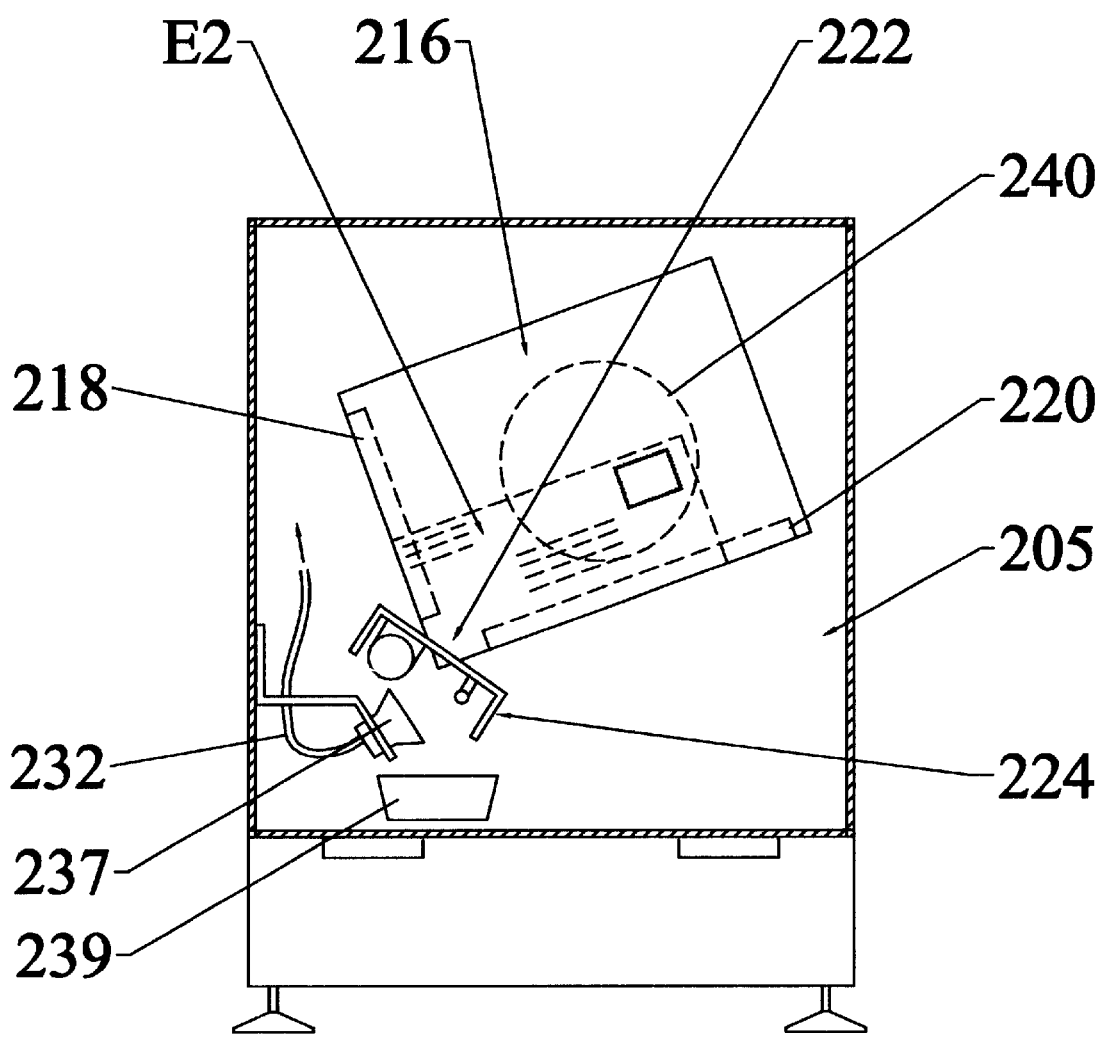
FIG. 11 is a sectional view of the parts and units on the inner side of the door in the direction of arrow XI—XI in FIG. 9.

FIGS. 9, 10, and 11 illustrate arrangement and mutual positions of parts and units inside the container 202. FIG. 9 is a top sectional view of the apparatus of FIG. 8 along the line IX—IX of FIG. 8, FIG. 10 is a side sectional view of the apparatus of FIG. 8 in the direction of lines X—X of FIG. 8, and FIG. 11 is view of the parts and units on the inner side of the door in the direction of line XI—XI in FIG. 9.

As shown in FIG. 10, the apparatus is provided with a door lock 206. The door lock 206 is provided with a solenoid 211, the core of which is located under the backside of the lock 206. Each time the door is closed, the solenoid 211 is activated, its core is raised and the door 204 is locked. In order to open the door 204, the operator pushes on a door-opening button 217 (FIG. 8). In the case the apparatus has detected a hazardous material, the solenoid 211 is deactivated, so that its core remains in raised up position and locks the door 204. This prevents the door of the apparatus from opening by a non-authorized person. For unlocking the door 204, the apparatus is provided with a key reset socket 213 located on the electronics compartment (FIG. 8) for a key reset switch 209 (shown in FIG. 8) accessible only to an authorized personnel.

As can be seen from FIGS. 10, 11, the inner side 205 (FIG. 11) of the door 204 supports an envelope-positioning unit 216 that consists of two mutually perpendicular slotted guide plates 218 and 220 which do not intersect and leave in an imaginary point of intersection a space 222 for positioning of the envelope corner. For convenience of insertion of the envelopes, the guide plates 218 and 220 may be inclined with respect to the vertical direction.

Figure 12:
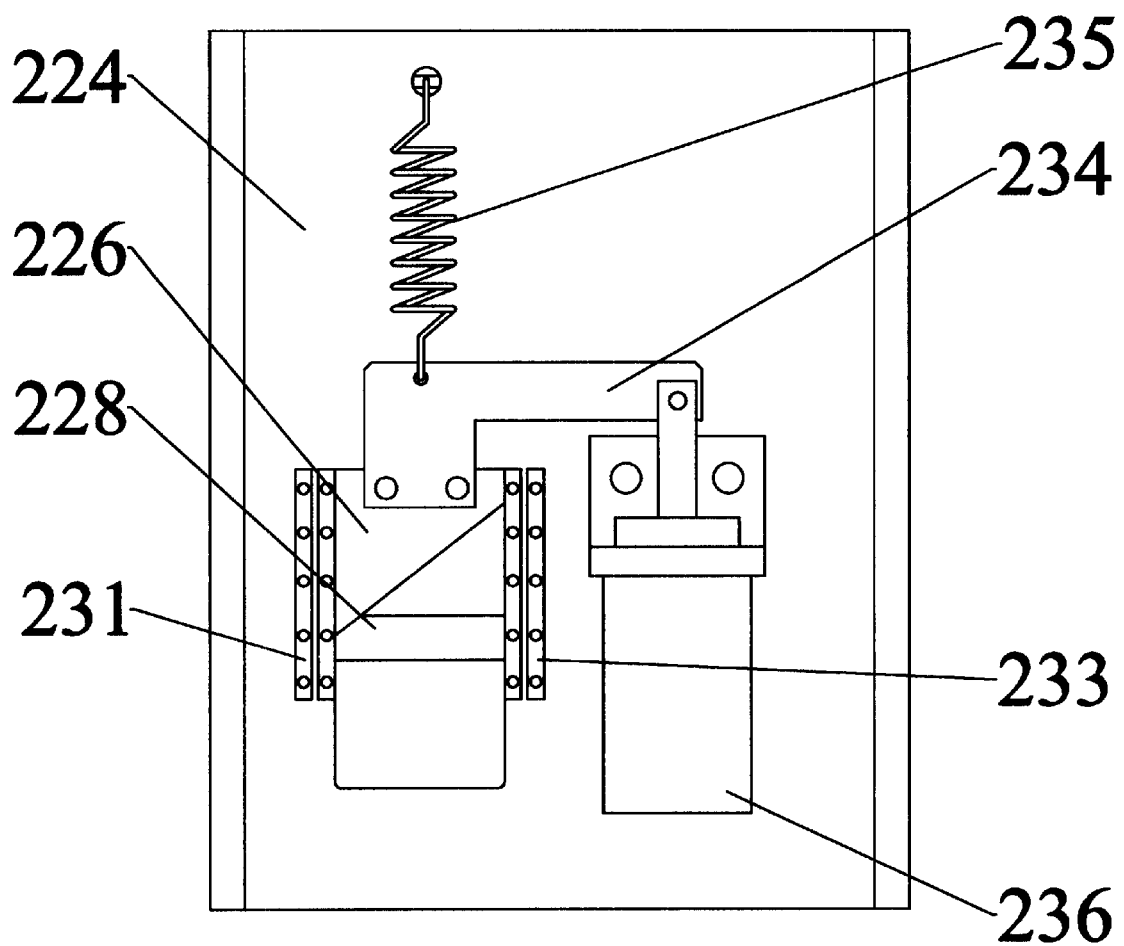
FIG. 12 is a schematic view of the envelope material remover used in the apparatus of FIGS. 8–11.

Located directly above the space 222, i.e., above the corner of the envelope E2 shown in FIG. 11 in the working position inside the envelope-positioning unit 216, is a guillotine-type envelope material remover 224, which is also attached to the inner side 205 of the door 204. A schematic view of the envelope material remover 224 is shown in FIG. 12. In this embodiment, the envelope material remover 224 consists of a moveable blade 226 and a stationary blade 228. The moveable blade 226 slides in two parallel guides 231 and 233 and is rigidly attached to one end of an L-shaped bracket 234, the other end of which is rigidly connected to an actuating mechanism, such as a pull-type solenoid 236. The bracket 234 is connected to a return spring 235 that normally maintains the moveable blade in the raised position. Activation of the solenoid 236 by pushing on the start button 210 (FIG. 8) will pull the solenoid core and hence the moveable blade 226 in the direction of the stationary blade 228. The path of the moveable blade 226 passes through the space 222 and hence through the corner of the envelope E2 (FIG. 11) placed into the envelope-positioning unit 216, whereby the corner of the envelope E2 is cut off.

As shown in FIG. 10, the apparatus 200 is provided with a powder detector 230, which in this embodiment is located inside the apparatus. Powder particles detection and evaluation means can include one or several of the following devices: particle counter counting the number of powder material particles, particle geometry analyzer analyzing the geometry of powder material particles, particle physical analyzer analyzing the physical properties of powder material particles, and particle chemical analyzer analyzing the chemical properties of powder material particles. For example, the powder detector 230 may be a standard portable particle counter, e.g., GT-321 type produced by Met One Instruments, Inc., Oregon, US. This small self-contained device is suitable for monitoring particle sizes from 0.3 microns to 5 microns in concentrations from 0 to 3,000,000 particles per cubic foot. It works on rechargeable batteries and incorporates a suction system.

The intake or suction tube 232 (FIG. 9) of the detector 230 has on its end a funnel-shaped suction cup 237 that is located directly under the cutting zone 222 (FIG. 11). The surface of the suction cup is coated with a thin filter for passing the powder and for preventing penetration of envelope cut-off debris into the detector.

Figure 13:
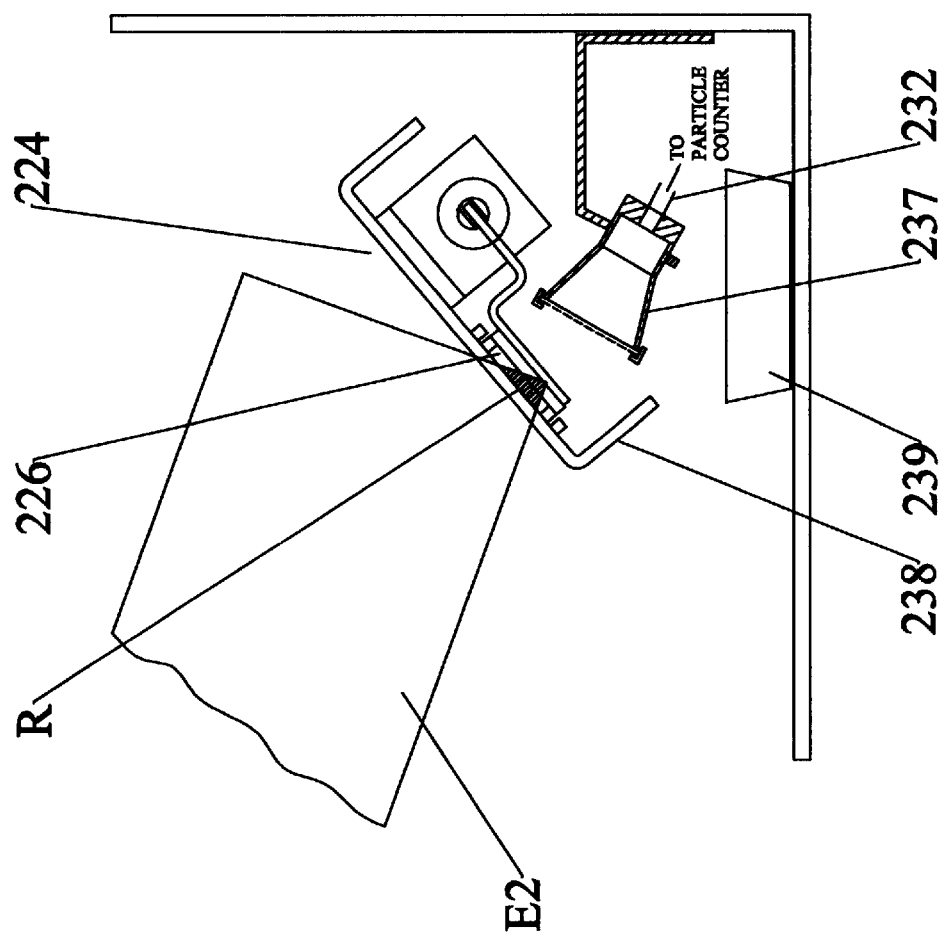
FIG. 13 is a fragmental view of the envelope cutting and powder suction zone of the apparatus of FIGS. 8–12.

FIG. 13 is a fragmental view of the envelope cutting and powder suction zone of the apparatus 200. As shown in FIGS. 11 and 13, the apparatus is provided with a debris collection tray 239 located directly under the cutter 224 and under the space 222 so that the debris, such as the cut off corner of the envelope E2, will fall into the debris collection tray 239. In order to direct the cut-off corner away from the suction cup 237 and into the tray 239, a guide plate 238 of the type shown in FIG. 13 is attached to the back side of the moveable blade so that when the moveable blade 225 approaches the cutting position, the guide plate also enters the space under the cutting zone for directing the debris to the tray 239.

An powder excitation and extraction unit 240 (FIGS. 9, 10, and 11) used in the apparatus of the embodiment is the same as the shaker 44 of the previous embodiment shown in FIGS. 2 and 3. The unit 240 is made in the form of an acoustic loudspeaker installed on a vertical compartment wall 241 (FIGS. 9 and 10) installed inside the container 202, so that the front vibrating surface of the loudspeaker that generates acoustic waves is located in close proximity to the envelope E2 placed into the envelope-positioning unit 216. The loudspeaker 240 is provided with an a.c. generator connected to the loudspeaker via an amplifier. The a.c. generator and the amplifier of this embodiment are not shown in the drawings and are located in the electronics compartment 203 (FIG. 8).

Figure 14:
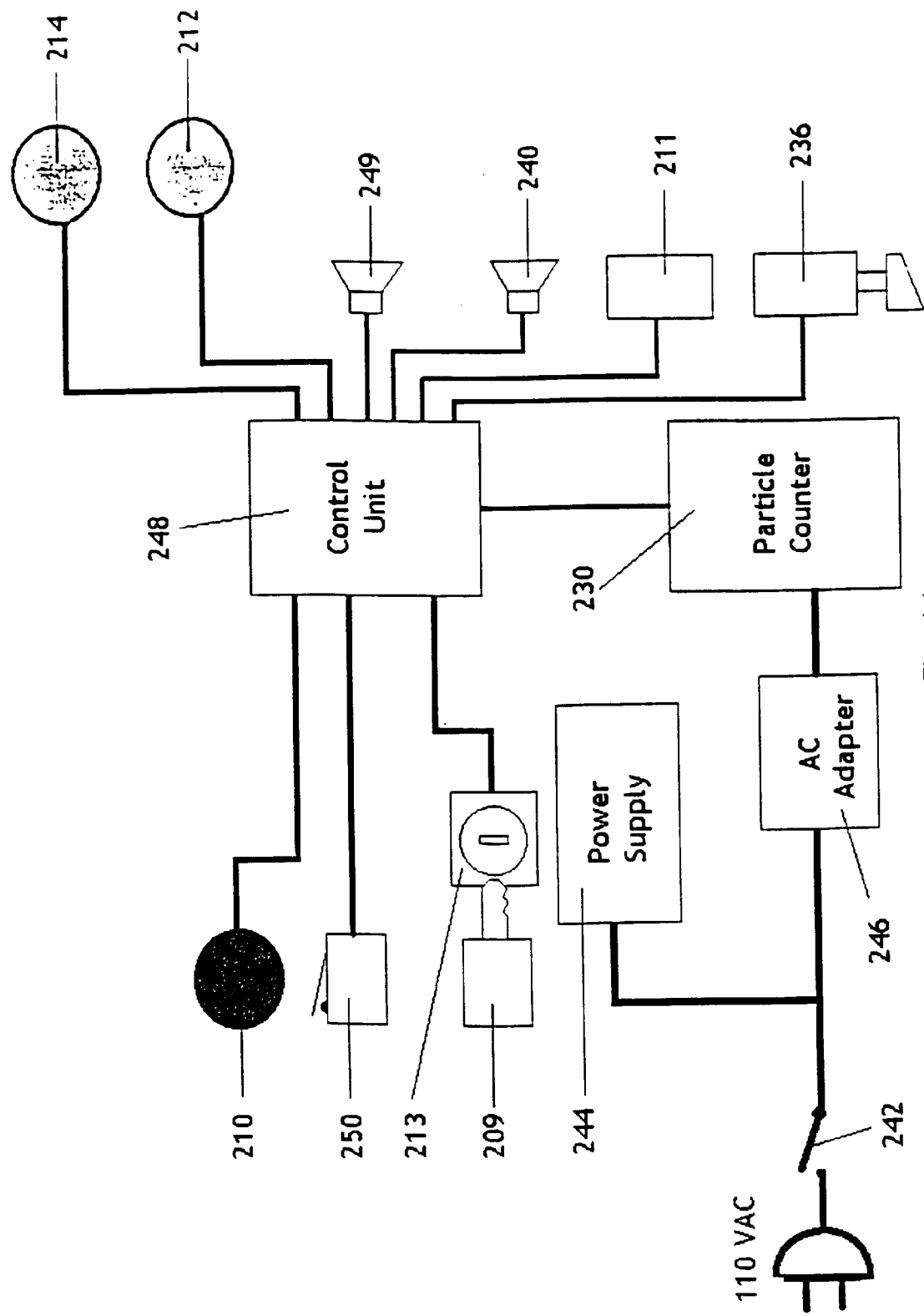
FIG. 14 is an electrical block diagram of the apparatus of the invention.

FIG. 14 is a block diagram of the control system of the apparatus of the invention. Through a general ON/OFF switch 242 the power supply unit 244 is connected to a conventional a.c. power network that supplies current to the cutter solenoid 236, the loudspeaker 240, and to the powder detector 230 via an AC/DC adapter 246 (electrical connections are not shown in FIG. 14). The powder detector 230 may operate from an accumulator battery as well. Control of the apparatus is carried out from a control unit 248 located inside the electronics compartment 203 (FIG. 8). More specifically, the control unit 248 controls operations of the alarm indicator lamp (red) 212, the normal operation status indicator lamp (green) 214, a warning sound speaker 249, the loudspeaker 240, the cutter solenoid 236, and the door lock solenoid 211. The apparatus is activated by pushing on a start button 210.

Reference numeral 250 designates a safety limit switch, which allows operation of the apparatus of the invention only when the container door is sealingly closed.

Operation of the Apparatus of the Invention

Either all incoming mail or only envelopes that may contain a suspicious substance are selected for checking in the apparatus of the invention. In the case of the embodiment described with reference to FIGS. 1–4, the operator opens the cover 24 located at the top of the container 22, and manually places a selected envelope into the envelope-positioning unit 36 so that the corner C of the envelope protrudes into the path of movement of the cutting blade 54 (FIG. 3). The operator then closes the cover 24 so that the interior of the container is sealed with a seal 26. The operator activates the solenoid 76 or 100 by pushing/pressing on the push button/pedal 78 (FIG. 3). The push button and pedal are also interlocked with activation of the excitation and extraction unit, so that the corner of the envelope is cut off, and at the same time the envelope is shaken with either the loudspeaker 44 (FIG. 3) or the plunger 88 (FIG. 4). The powder excitation and extraction unit 44 causes at least a part of the powder material to separate from the envelope and to leave the envelope with an air flow through the opening produced by cutting.

If the envelope contains a powdered material, this material will be sucked under the effect of the vacuum pump 72 into the powder detector 66 via the suction cup 74 and the supply tube 68. Depending on the type of the powder detector 66, the particles of the powder can be merely counted or analyzed, and the results of the analysis or count are compared with a predetermined value. In case the number of particles exceeds the preselected value or the results of analysis coincides with the preselected reference value, the apparatus generates an alarm signal warning the operator about the event of detection. If necessary, in this case the entire apparatus can be transported to another location for further analysis of the detected material and for appropriate treatment.

In the embodiment of FIG. 5, the cover is opened, the operator manually positions the envelope E in the envelope-positioning unit 108, the cover is closed, and the container is sealed. The operator then inserts the hands into the gloves 104a and 104b for repositioning of the envelope, if necessary, and pushes on two buttons 112a and 112b simultaneously (as a safety measure) for activation of the an envelope material removal device selected from a group consisting from cutting, punching, perforating, puncturing and tearing devices (not shown in FIG. 5). Pushing only on one button will not activate the envelope material removal device.

The device of the embodiment shown in FIGS. 6 and 7 may incorporate all the features of the previous embodiments and therefore operates in the same manner as described above. The only difference is that the envelope material removal device 114 consists of a plurality of cutting or punching rods 114a, 114b, . . . 114n and that the envelope is positioned in the envelope-positioning unit 116 so that a narrow edge of the envelope E1 projects into the path of the cutter. As a result, after activation of the envelope material removal device 114, the latter discretely perforates the edge of the envelope. The edge perforated as shown in FIG. 7 allows the powder to leave the envelope while the rest of the contents of the envelope remains inside the envelope.

Referring now to the embodiment shown in FIGS. 8–14, it should be noted that many features shown and described in connection with this embodiment, such as electronics compartment, safety lock of the door, a keylock feature, etc., could be incorporated into the embodiments of FIGS. 1–7 as well. Therefore, it should be assumed that description of operation of these features in connection with the embodiment of FIGS. 8–14 should be associated also with the embodiments of FIGS. 1–7.

The operator opens the door 204 located at the front side of the container 202 by pushing on the door-opening button 217. This action activates the solenoid 211 (FIG. 10), the core of this solenoid is pulled into the coil and releases the lock 206 for opening the door. The operator manually places a selected envelope E2 (FIGS. 11 and 13) into the envelope-positioning unit 216 so that the corner R of the envelope E2 protrudes into the path of movement of the moveable blade 226. The operator then closes the door 204 so that the interior of the container is sealed. By pushing on the start button 210, the operator initiates a sequence of operations consisting in activation of the solenoid 236 of the envelope material removal device (FIG. 12), cutting the protruding corner R of the envelope (FIG. 13), and activating the loudspeaker 240 (FIGS. 10 and 14). Pushing on the start button 210 also activates the powder detector 230 located inside the container (FIGS. 9 and 10).

As the moveable blade 226 moves down while performing its cutting stroke, it lowers the debris guiding plate 238 into a position in which it directs the cut-off corner of the envelope to the tray 239 (FIG. 13).

If the envelope E2 contains a powdered material, this material will be sucked into the powder suction cup 237 (FIG. 13) located near the cutting zone. Depending on the type of the powder detector 230, the particles of the powder can be merely counted or analyzed, and the results of the analysis or count are compared with a predetermined value. In case the number of particles exceeds the preselected value or the results of analysis coincides with the preselected reference value, the apparatus generates an alarm signal warning the operator about the event of detection. More specifically, the control unit 248 stores predetermined data corresponding to different types of powdered materials, compares the results of measurements with this data, and generates comparison data used for judgment on the presence or absence of the powdered material.

The alarm signal, which is generated in response to the aforementioned comparison data, deactivates the solenoid 211, and this action blocks the lock 206 thus preventing the door 204 from opening by non-authorized personnel. In this case the door 204 can be opened only by an authorized person with the use of a special reset key 209 (FIG. 8). If necessary, in this case the entire apparatus can be easily transported to another location for further analysis of the detected material and for appropriate treatment.

Thus it has been shown that the invention provides a method and apparatus for revealing mail with suspicious contents as a measure of preliminary presorting of closed postal envelopes and for making the mail with a suspicious substance available for a further detailed analysis. The invention provides an apparatus simple in construction, inexpensive to manufacture, simple and safe in use, and incorporating a commercially produced particle detector. The invention also provides the aforementioned apparatus and method suitable for use in mailrooms of enterprises and companies that daily receive from several to thousands items of mail.

Although the invention has been shown and described with reference to specific embodiments, it is understood that these embodiments should not be construed as limiting the areas of application of the invention and that any changes and modifications are possible, provided these changes and modifications do not depart from the scope of the attached patent claims. For example, powder detectors of the types different from those shown and described in the specification may be suitable for use in conjunction with the apparatus and method of the invention. The cover of the container may have a slot located above the envelope-positioning unit for dropping the envelopes into the converging guides of the aforementioned envelope-positioning unit for self-orientation. The display of the powder detector may be located in a place remote from the apparatus. The powder detector can be provided with various adjustable alarm systems responding to the type of powder found in the envelopes. The powder excitation and extraction units may be of the types different from those shown and described and provided with means for adjusting the mode of operation to match with the types of the envelopes processed in the apparatus of the invention. It is understood that the cutter for perforation of the envelope edge can also be used in conjunction with operating units of the embodiment of FIGS. 8–14. The envelope material removal device may be different from the guillotine type and include punching, perforating, puncturing or tearing components, removal of the envelope material by etching, laser treatment, etc. The safety lock mechanism can be installed on the container cover as well.

What is claimed is:

1. An apparatus for detecting the presence of powdered material in envelopes comprising:

a container with means for opening and sealingly closing said container;

an envelope material removal device selected from a group consisting from a cutting device, a punching device and a perforating device, with a moveable member;

positioning means for positioning at least a part of said envelope in the path of movement of said moveable member;

a powder excitation and extraction means for shaking said envelope and contents thereof and for extracting at least a part of said powdered material from said envelope;

a powder detector having suction means for sucking said powdered material and particle evaluation means for determining characteristics of said powdered material; and control means for making a decision on the presence of said powdered material.

2. The apparatus of claim 1, wherein said moveable member is selected from a group consisting of a continuous cutting member that produces a continuous cut in said at least part of said envelope, a discrete punching member that produces an intermittent punch in said at least part of said envelope, and a continuous punching member that produces a continuous hole in said at least part of said envelope.

3. The apparatus of claim 2, wherein said positioning means comprise a pair of substantially mutually perpendicular guide plates with guide slots for edges of said envelope, said guide plates forming an open space for projection of said at least a part of said envelope to said path of movement of said moveable member.

4. The apparatus of claim 3, wherein said powder excitations and extraction means is selected from a group consisting of vibration means and impact means.

5. The apparatus of claim 4, wherein said vibration means is a loudspeaker spaced from said envelope at a distance that allows transmission of acoustic vibrations to said envelope from said loudspeaker for excitation and extraction of the contents of said envelope.

6. The apparatus of claim 4, wherein said impact means comprise a plunger and a plunger drive means for driving said plunger for transmitting impacts to said envelope.

7. The apparatus of claim 6, wherein said plunger drive means comprises a first solenoid.

8. The apparatus of claim 2, wherein said material removal device has drive means in the form of a second solenoid.

9. The apparatus of claim 7, wherein said material removal device has drive means in the form of a second solenoid, said apparatus further comprising an operation starting means selected from a group consisting of a push button and a foot pedal, said operation starting means being electrically connected at least to one of said first solenoid and said second solenoid.

10. The apparatus of claim 4, wherein said at least a part of said envelope is selected from at least one envelope corner and at least a part of at least one envelope edge.

11. The apparatus of claim 4, wherein said container has at least one transparent surface, said envelope positioning means comprising flexible gloves sealingly inserted into said container and seen through said transparent surface.

12. The apparatus of claim 11, further comprising an operation starting means in the form of a foot pedal electrically connected to said powder excitation and extraction means.

13. The apparatus of claim 2, wherein said means for opening and sealingly closing said container is a door hinged to said container, said envelope material removal device and said envelope positioning means being installed on said door and inside of said container when said door is closed, said moveable member being selected from a group consisting of a continuous cutting member that produces a continuous cut in said envelope and a discrete punching member that produces an intermittent cut in said envelope.

14. The apparatus of claim 13, wherein said positioning means comprise a pair of substantially mutually perpendicular guide plates with guide slots for edges of said envelope, said guide plates forming an open space for projection of said at least a part of said envelope to said path of movement of said moveable member.

15. The apparatus of claim 14, wherein said powder excitation and extraction means is selected from a group consisting of vibration means and impact means.

16. The apparatus of claim 15, wherein said vibration means is a loudspeaker spaced from said envelope at a distance that allows transmission of acoustic vibrations to said envelope from said loudspeaker for excitation and extraction of the contents of said envelope.

17. The apparatus of claim 15, wherein said impact means comprise a plunger and a plunger drive means for driving said plunger for transmitting impacts to said envelope.

18. The apparatus of claim 17, wherein said plunger drive means comprises a first solenoid.

19. The apparatus of claim 13, wherein said material removal device has drive means in the form of a second solenoid.

20. The apparatus of claim 18, wherein said material removal device has drive means in the form of a second solenoid, said apparatus further comprising an operation starting means selected from a group consisting of a push button and a foot pedal, said operation starting means being electrically connected at least to one of said first solenoid and said second solenoid.

21. The apparatus of claim 13, wherein said at least a part of said envelope is selected from at least one envelope corner and at least a part of at least one envelope edge.

22. The apparatus of claim 2, further provided with a cutting debris collecting tray position under said path of movement of said moveable member and cutting debris guide plate attached to said moveable member and positioned during cutting above said cutting debris collecting tray for directing the cutting debris into said cutting debris collecting tray.

23. The apparatus of claim 13, further provided with a cutting debris collecting tray position under said path of movement of said moveable member and cutting debris guide plate attached to said moveable member and positioned during cutting above said cutting debris collecting tray for directing the cutting debris into said cutting debris collecting tray.

24. The apparatus of claim 2, further comprising a comparison means for comparing results of said evaluation with a predetermined value for obtaining a comparison data; and alarm means for generating an alarm signal in response to said comparison data.

25. The apparatus of claim 11, further comprising a comparison means for comparing results of said evaluation with a predetermined value for obtaining a comparison data; and alarm means for generating an alarm signal in response to said comparison data.

26. The apparatus of claim 13, further comprising a comparison means for comparing results of said evaluation with a predetermined value for obtaining a comparison data; and alarm means for generating an alarm signal in response to said comparison data.

27. The apparatus of claim 26, further comprising a door lock mechanism provided with a third solenoid, which blocks said door from opening in case of activation of said alarm means.

28. The apparatus of claim 27, further provided with a key for unlocking said door lock.

29. The apparatus of claim 2, wherein said particle evaluation means are selected from a group consisting of particle counter counting the number of powder material particles, particle geometry analyzer analyzing the geometry of powder material particles, particle physical analyzer analyzing the physical properties of powder material particles, and particle chemical analyzer analyzing the chemical properties of powder material particles.

30. The apparatus of claim 10, wherein said particle evaluation means are selected from a group consisting of particle counter counting the number of powder material particles, particle geometry analyzer analyzing the geometry of powder material particles, particle physical analyzer analyzing the physical properties of powder material particles, and particle chemical analyzer analyzing the chemical properties of powder material particles.

31. The apparatus of claim 25, wherein said particle evaluation means are selected from a group consisting of particle counter counting the number of powder material particles, particle geometry analyzer analyzing the geometry of powder material particles, particle physical analyzer analyzing the physical properties of powder material particles, and particle chemical analyzer analyzing the chemical properties of powder material particles.

32. The apparatus of claim 13, wherein said particle evaluation means are selected from a group consisting of particle counter counting the number of powder material particles, particle geometry analyzer analyzing the geometry of powder material particles, particle physical analyzer analyzing the physical properties of powder material particles, and particle chemical analyzer analyzing the chemical properties of powder material particles.

33. The apparatus of claim 24, wherein said particle evaluation means are selected from a group consisting of particle counter counting the number of powder material particles, particle geometry analyzer analyzing the geometry of powder material particles, particle physical analyzer analyzing the physical properties of powder material particles, and particle chemical analyzer analyzing the chemical properties of powder material particles.

34. The apparatus of claim 26, wherein said particle evaluation means are selected from a group consisting of particle counter counting the number of powder material particles, particle geometry analyzer analyzing the geometry of powder material particles, particle physical analyzer analyzing the physical properties of powder material particles, and particle chemical analyzer analyzing the chemical properties of powder material particles.

35. A method for detecting a powdered material in an envelope comprising the steps of:

providing a powder detection apparatus comprising a container, an envelope positioning means in said container for exposing at least a part of said envelope to form an exposed part of said envelope, an envelope material removal means in said container with a moveable member having a path passing through said exposed part of said envelope, a powder excitation and extraction means, and a powder detection means;

placing said envelope into said envelope positioning means for positioning said exposed part in the path of said moveable member;

separating at least a part of said exposed part from said envelope by an envelope material removal method selected from a group of cutting, perforating, punching, puncturing and tearing;

exciting said powdered material in said envelope with said powder excitation and extraction means for causing at least a part of said powdered material to leave said envelope;

supplying said at least part of said powdered material to said powder detection means by suction air that contains at least a part of said powdered material; and detecting said powdered material with said powder detection means.

36. The method of claim 35, wherein said powder detection means comprises a particle counter for counting the number of particles in a unit of volume of said air, said method further comprising the step of counting the number of particles in a unit of volume of said air.

37. The method of claim 36, wherein said powder detector means further comprises a powder analysis means, said method further comprising the steps of analyzing the powder particles, comparing the powder analysis data with at least one predetermined reference data, and generating an alarm signal in response to said step of comparing.

38. The method of claim 35, wherein said step of separating of a part of said exposed part is cutting off a corner of said envelope.

39. The method of claim 35, wherein said step of separating of a part of said exposed part is punching at least one hole in said envelope.

40. The method of claim 35, wherein said powder excitation and extraction means is selected from the group consisting of acoustic vibrations and mechanical impacts, and said step of exciting said powdered material comprises a process selected from acoustically vibrating and mechanically impacting said envelope.

* * * * *